(12) United States Patent
Bäck

(10) Patent No.: US 10,687,990 B2
(45) Date of Patent: Jun. 23, 2020

(54) DISPOSABLE PANT-TYPE ABSORBENT ARTICLE

(71) Applicant: Essity Hygiene and Health Aktiebolag, Göteborg (SE)

(72) Inventor: Lucas Bäck, Göteborg (SE)

(73) Assignee: ESSITY HYGIENE AND HEALTH AKTIEBOLAG, Göteborg (SE)

(*) Notice: Subject to any disclaimer, the term of this patent is extended or adjusted under 35 U.S.C. 154(b) by 0 days.

(21) Appl. No.: 16/462,384

(22) PCT Filed: Nov. 30, 2016

(86) PCT No.: PCT/SE2016/051193
§ 371 (c)(1),
(2) Date: May 20, 2019

(87) PCT Pub. No.: WO2018/097776
PCT Pub. Date: May 31, 2018

(65) Prior Publication Data

US 2019/0314216 A1    Oct. 17, 2019

(30) Foreign Application Priority Data

Nov. 23, 2016   (WO) ............... PCT/SE2016/051157

(51) Int. Cl.
*A61F 13/49*        (2006.01)
*A61F 13/491*       (2006.01)
(Continued)

(52) U.S. Cl.
CPC ...... *A61F 13/491* (2013.01); *A61F 13/15593* (2013.01); *A61F 13/49001* (2013.01);
(Continued)

(58) Field of Classification Search
CPC .......... A61F 13/49011; A61F 13/49012; A61F 13/49061; A61F 13/496;
(Continued)

(56) References Cited

U.S. PATENT DOCUMENTS

| 8,980,040 B2 | 3/2015 | Gouda et al. |
| 2013/0211363 A1 | 8/2013 | LaVon et al. |
| 2017/0065463 A1* | 3/2017 | Mori ................. A61F 13/15747 |

FOREIGN PATENT DOCUMENTS

| EA | 201200967 A1 | 1/2013 |
| EP | 2260811 A1 | 12/2010 |

(Continued)

OTHER PUBLICATIONS

International Search Report and Written Opinion for International Application No. PCT/SE2016/051193, dated Jun. 22, 2017—14 pages.

(Continued)

*Primary Examiner* — Catharine L Anderson
(74) *Attorney, Agent, or Firm* — Buchanan Ingersoll & Rooney P.C.

(57) ABSTRACT

The disclosure relates to a disposable pant-type absorbent article, such as a pant diaper, a sanitary pant or incontinence pant, for an adult user. The absorbent article has a longitudinal direction (Y) and a transverse direction (X). The absorbent article includes a front body panel having a first at least partly elastic region extending along leg edges of the front body panel, and a second at least partly elastic region located next to the first elastic region. A back body panel has a third elastic region extending at least partly over the buttocks-covering section of the back body panel. Each of the elastic regions is elasticised by means of a plurality of elastic threads arranged substantially in the transverse direction across a major portion of the front or back body panel. A side edge of the third elastic region overlaps in the (Continued)

longitudinal direction both a side edge of the first at least partly elastic region and part of a side edge of the second at least partly elastic region at the side seams.

29 Claims, 3 Drawing Sheets

(51) Int. Cl.
*A61F 13/15* (2006.01)
*A61F 13/496* (2006.01)
*A61F 13/511* (2006.01)
*A61F 13/514* (2006.01)
*A61F 13/53* (2006.01)

(52) U.S. Cl.
CPC ...... *A61F 13/496* (2013.01); *A61F 13/49011* (2013.01); *A61F 13/49012* (2013.01); *A61F 13/4915* (2013.01); *A61F 13/511* (2013.01); *A61F 13/514* (2013.01); *A61F 13/53* (2013.01); *A61F 2013/49025* (2013.01); *A61F 2013/49026* (2013.01); *A61F 2013/49028* (2013.01); *A61F 2013/49074* (2013.01); *A61F 2013/49084* (2013.01)

(58) Field of Classification Search
CPC .. A61F 2013/49025; A61F 2013/49026; A61F 2013/49028; A61F 2013/49071; A61F 2013/49074
See application file for complete search history.

(56) References Cited

FOREIGN PATENT DOCUMENTS

| EP | 2529715 A1 | 12/2012 | |
|----|----|----|----|
| EP | 2556809 A1 | 2/2013 | |
| EP | 2561846 A1 | 2/2013 | |
| WO | 2014098683 A1 | 6/2014 | |
| WO | WO-2015137129 A1 * | 9/2015 | ....... A61F 13/15723 |
| WO | 2016029372 A1 | 3/2016 | |

OTHER PUBLICATIONS

International Preliminary Report on Patentability for International Application No. PCT/SE2016/051193, dated Nov. 8, 2018—6 pages.
Russian Office Action for Russian Application No. 2019119376/12(037464), dated Dec. 19, 2019 with translation, 9 pages.

* cited by examiner

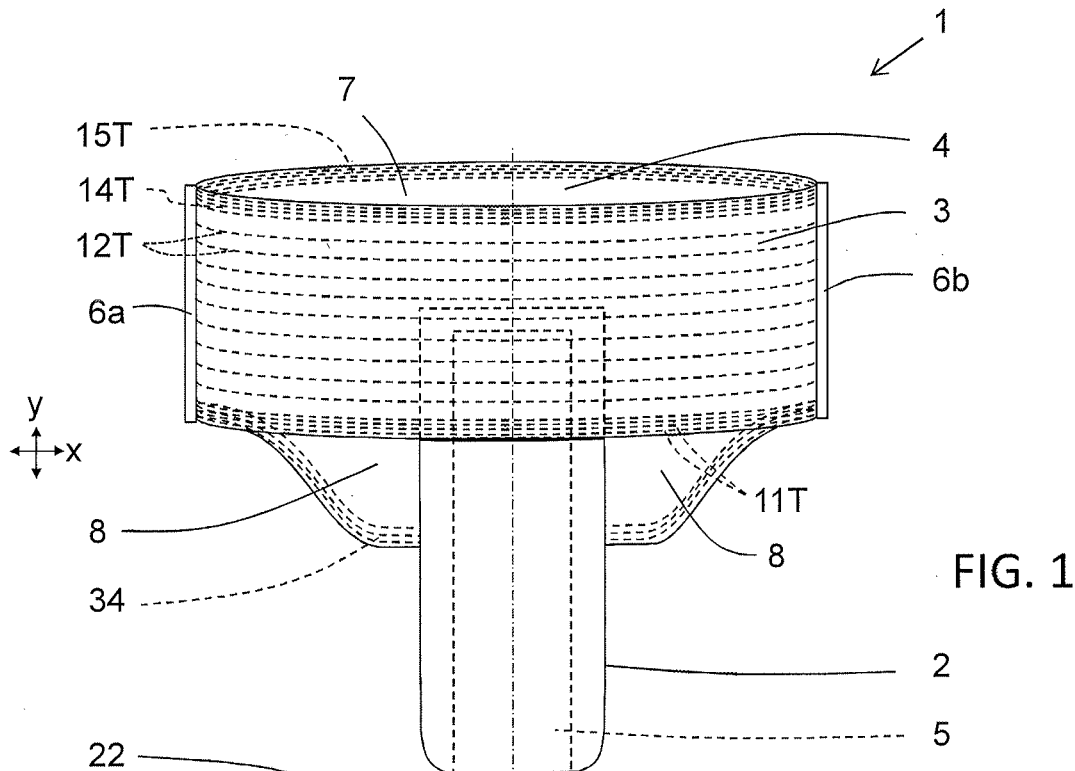
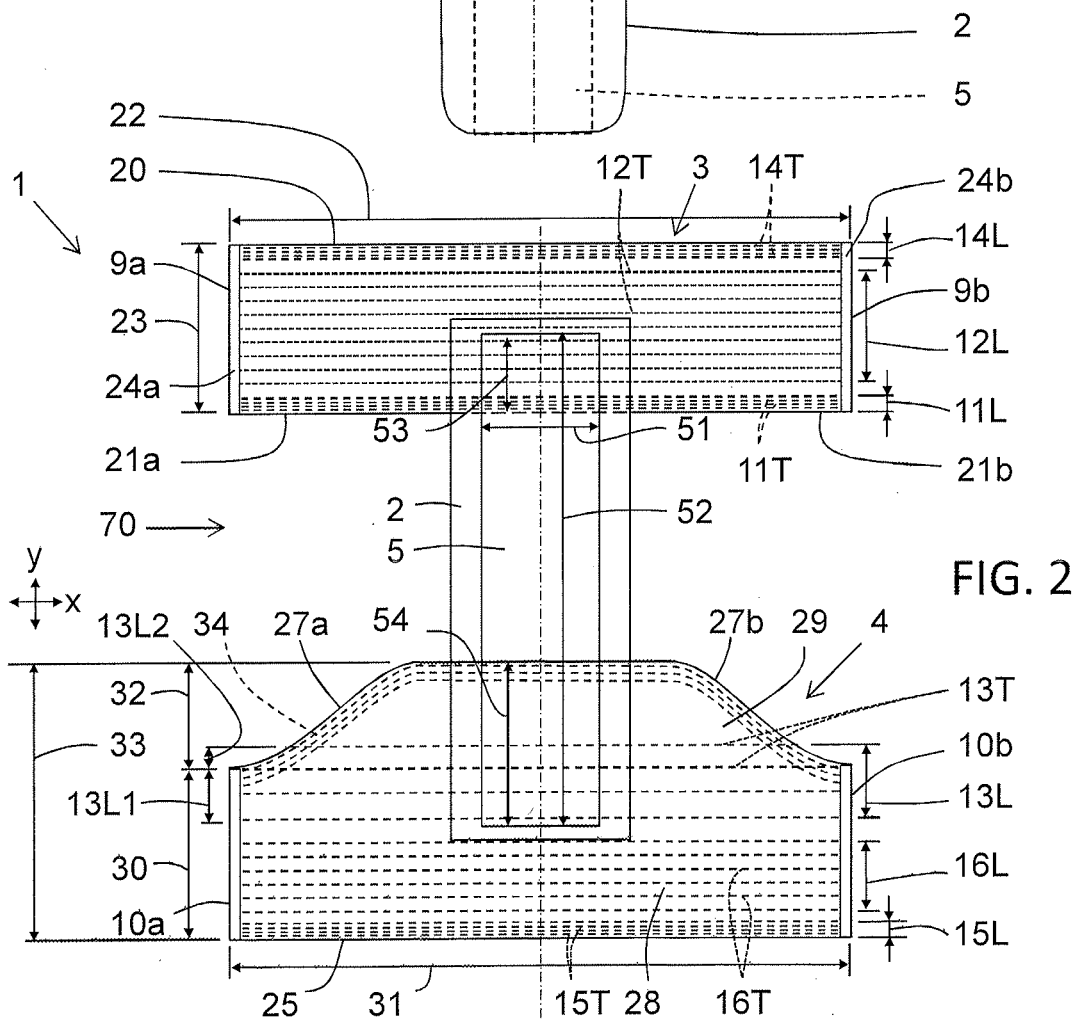
FIG. 1
FIG. 2

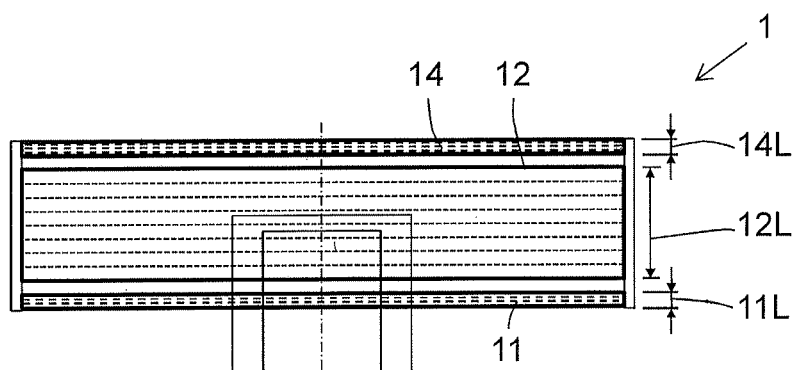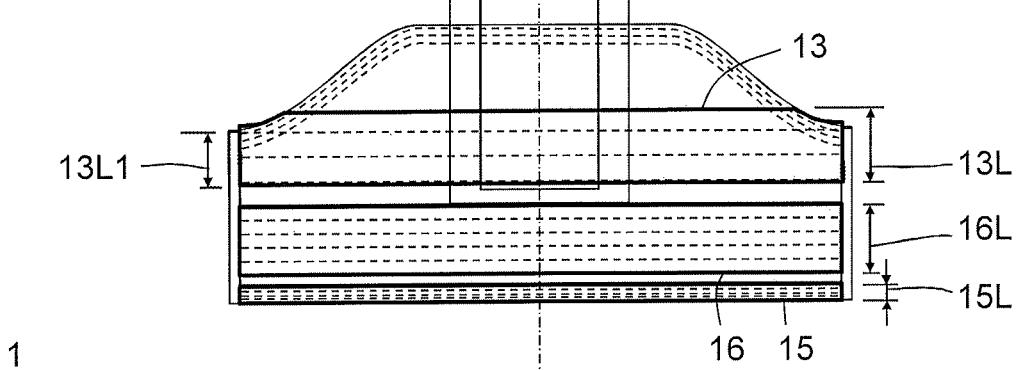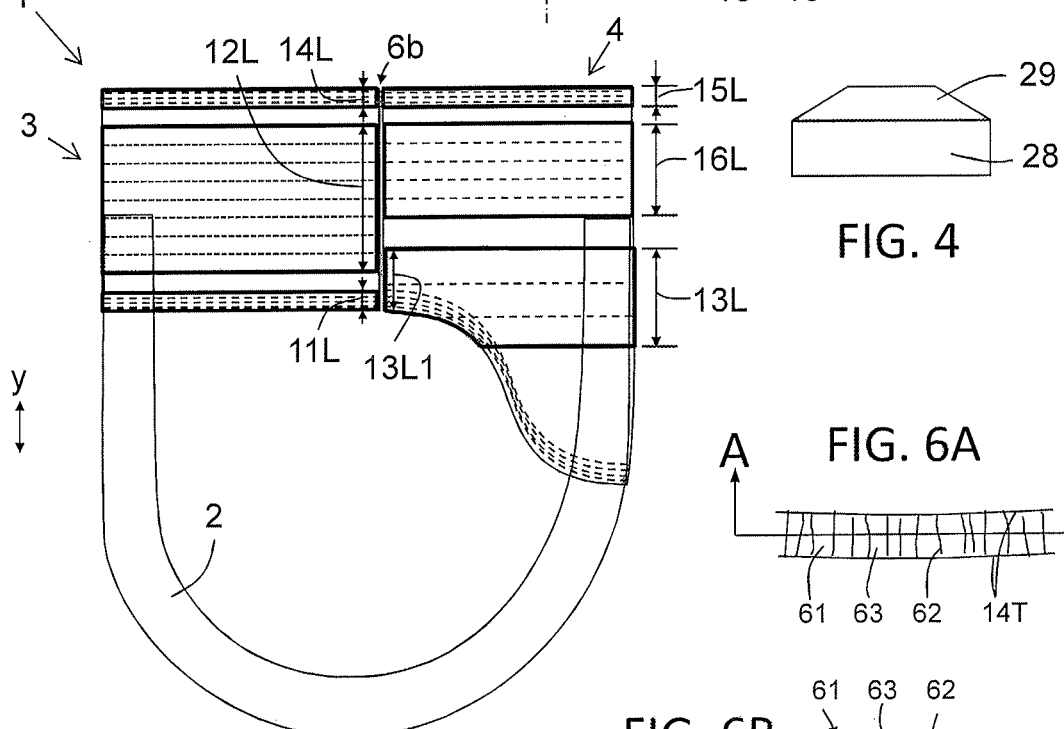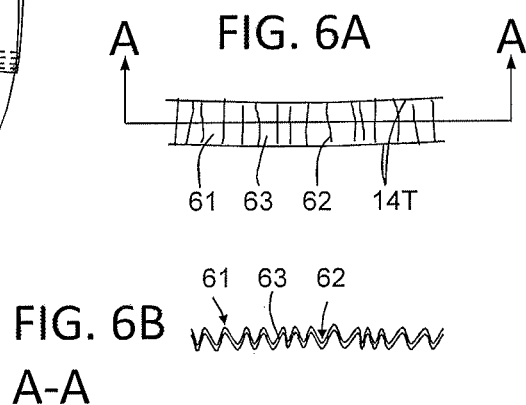

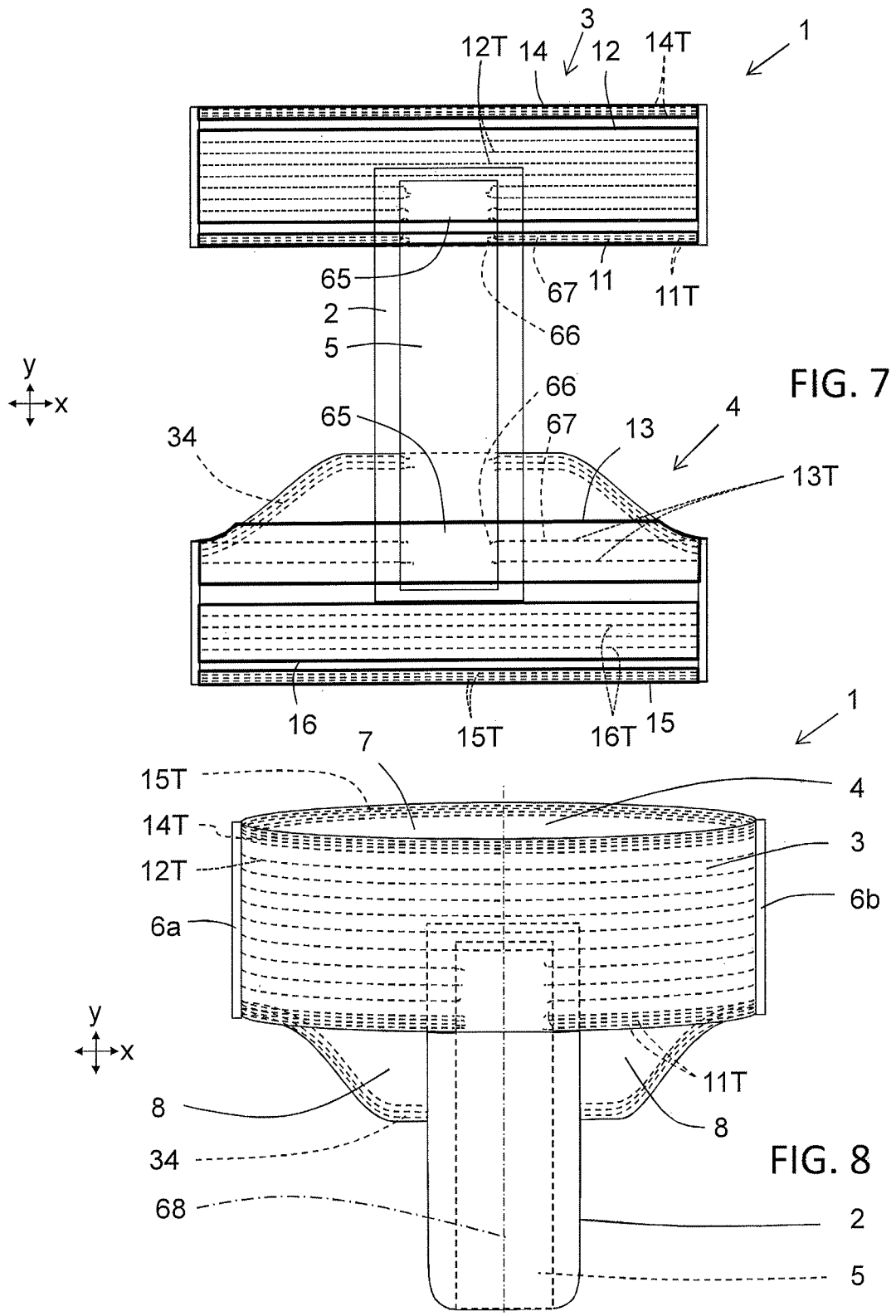

DISPOSABLE PANT-TYPE ABSORBENT ARTICLE

CROSS REFERENCE TO RELATED APPLICATIONS

This is a U.S. National Phase application of PCT/SE2016/051193, filed Nov. 30, 2016, which claims priority to PCT/SE2016/051157, filed Nov. 23, 2016, the disclosures of each application being incorporated herein by reference in their entireties for all purposes.

TECHNICAL FIELD

This disclosure relates to disposable pant-type absorbent article, such as a pant diaper, a sanitary pant or incontinence pant, for an adult user. The pant-type absorbent article comprises a front body panel, a back body panel, and an absorbent insert located mainly in a crotch portion of the article and connected to the front and back body panels for bridging the gap between the front and back body panels, wherein the absorbent insert comprises an absorbent core. The disposable pant-type absorbent article according to the disclosure is intended for both male and female users, and may be provided in various sizes.

BACKGROUND

There is general desire in the field of disposable pant-type absorbent articles to provide absorbent articles with increased comfort and fit and discrete underwear-like visual appearance. For example, document EP 2 260 811 A1 discloses a disposable diaper with alleged good appearance. However, further improvement in terms of comfort, fit and discrete underwear-like visual appearance is desirable.

SUMMARY

An object of the present disclosure is to provide a disposable pant-type absorbent article with further increased comfort and fit and discrete underwear-like visual appearance. This object is at least partly achieved by the features of claim 1.

The disclosure concerns a disposable pant-type absorbent article, such as a pant diaper, a sanitary pant or incontinence pant, for an adult user. The absorbent article has a longitudinal direction and a transverse direction and comprises
- a front body panel having a waist edge, a pair of leg edges and a pair of side edges,
- a back body panel having waist edge, a pair of leg edges, a pair of side edges, a main section and a buttocks-covering section, and
- an absorbent insert located mainly in a crotch portion of the article and connected to the front and back body panels for bridging the gap between the front and back body panels, wherein the absorbent insert comprises an absorbent core.

The front and back body panels are joined to each other at opposite side edges to at least partly define a waist-opening and a pair of leg-openings. The front body panel has a first at least partly elastic region extending along the leg edges of the front body panel, and a second at least partly elastic region located next to the first elastic region. The back body panel has a third elastic region extending at least partly over the buttocks-covering section of the back body panel. Each of said elastic regions are elasticised by means of a plurality of elastic threads arranged substantially in the transverse direction across a major portion of the front or back body panel. A side edge of the third elastic region overlaps in the longitudinal direction both a side edge of the first at least partly elastic region and part of a side edge of the second at least partly elastic region at the side seams.

By implementing an overlap in the longitudinal direction of the side edge of the third elastic region with both the side edge of the first at least partly elastic region and part of a side edge of the second at least partly elastic region, in the area of the side seams, the third elastic region, which extends into the buttocks-covering section is extended in the longitudinal direction towards the waist region, thereby accomplishing a relatively large third elastic region. Moreover, since the third elastic region extends into the buttocks-covering section, which generally has a relatively large elasticity and flexibility for improved fit, the relatively large elasticity and flexibility is provided also up into a lower side seam area of the back body panel. In all, the subject-matter of claim 1 results in a disposable pant-type absorbent article with increased comfort and fit.

The front body panel may further have a fourth elastic region extending along the waist-edge of the front body panel, wherein the second at least partly elastic region is located between the first and fourth elastic regions. The fourth elastic region extending along the waist-edge of the front body panel enables a specifically selected contractile force per unit area for the waist of the absorbent article, thereby enabling further improved fit and discrete underwear-like visual appearance.

The back body panel may further comprise a fifth elastic region extending along the waist-edge of the back body panel. The fifth elastic region extending along the waist-edge of the back body panel enables a specifically selected contractile force per unit area for the waist of the absorbent article, thereby enabling further improved fit and discrete underwear-like visual appearance.

The back body panel may further have a sixth elastic region located between the third and fifth elastic regions. Increased division of the back body panel into smaller regions enables further shaping of the absorbent article to better fit the shape of the human body, thereby enabling further improved comfort, fit and discrete underwear-like visual appearance.

A side edge of the third elastic region may overlap about 15 to 80 millimetres, specifically about 25 to 65 millimetres, as seen in the longitudinal direction, with the side seams of the absorbent article. As mentioned above, by having the third elastic region extending into the buttocks-covering section as well as up into the lower side seam area of the back body panel, the relatively large elasticity and flexibility associated with the buttock-covering section is also true for the lower side seam area of the back body panel for increased comfort and fit.

The third elastic region may extend about 15 to 80 millimetres, specifically about 25 to 65 millimetres, as seen in the longitudinal direction, into the buttocks-covering section. A certain level of elasticity of the laminated web material is advantageous also in the buttocks-section for improved fit and comfort.

A length of the buttocks-covering section in the longitudinal direction may be in the range of 25 to 60%, specifically 35% to 50%, of the maximal length of the back body panel in the longitudinal direction.

The sixth elastic region may be selected to not overlap with the absorbent core more than 40 millimetres in the longitudinal direction, specifically not more than 20 millimetres. The sixth elastic region typically has a higher contractile force per unit area than the third elastic region, such that a significant overlap of the sixth elastic region with absorbent core may have negative effect of the absorption capacity of the absorbent core due to a relatively strong compression effect exerted by the sixth elastic region on the absorbent core.

A side edge of the first at least partly elastic region may have an extension of about 5 to 20 millimetres, specifically about 8 to 17 millimetres, as seen in the longitudinal direction. A distinct waist elastic of the front body panel typically results in improved comfort, fit and discrete underwear-like visual appearance.

The front body panel may have a substantially rectangular shape. A rectangular shape front body panel enables cost-efficient manufacturing because all elastic threads of the front body panel may also be arranged in the transverse direction of the absorbent article, i.e. along the machine direction in the manufacturing machine. Straight elastic threads requires less complex manufacturing equipment and the adhesive for securing the elastic threads may be supplied directly on the elastic threads before laminating the sheets of web material and elastic threads together to form body panels. Moreover, the rectangular shaped front body panel also enables manufacturing with low level of scrap material caused for example by cutting out complex two-dimensional shapes from a sheet of laminated web material.

The back body panel may have a shape composed of a substantially rectangular shaped main section intended to be located towards a waist of a user and a substantially trapezoid shaped buttocks-covering section intended to be located towards a crotch of a user. A substantially trapezoid shaped buttocks-covering section provides improved fit and comfort to a user, as well as improved underwear-like visual appearance.

The fourth elastic region may comprise 4 to 6 elastic threads. This number of elastic threads enables underwear-like waist elastic of the absorbent article.

The fourth elastic region may comprise a plurality of elastic threads arranged parallel at substantially equally spaced intervals of 2 to 8 millimetres. The relatively small intervals provide underwear-like visual appearance in the waist region of the front body panel.

The second at least partly elastic region may comprise 9 to 18 elastic threads. The second elastic region typically corresponds to the belly portion of the absorbent article, and a relatively large number of elastic threads enable a large and comfortable belly portion.

The second at least partly elastic region may comprise a plurality of elastic threads arranged parallel at substantially equally spaced intervals of 5 to 13 millimetres. Having relatively large intervals between neighbouring elastic threads in a belly portion of absorbent article enables a large and comfortable belly portion.

The first at least partly elastic region may comprise 4 to 6 elastic threads. This number of elastic threads enables underwear-like leg elastic of the absorbent article.

The first at least partly elastic region may comprise a plurality of elastic threads arranged parallel at substantially equally spaced intervals of 2 to 8 millimetres. The relatively small intervals provide underwear-like visual appearance in the leg region of the front body panel.

The fifth elastic region may comprise 4 to 6 elastic threads. This number of elastic threads enables underwear-like waist elastic of the absorbent article.

The fifth elastic region may comprise a plurality of elastic threads arranged parallel at substantially equally spaced intervals of 2 to 8 millimetres. The relatively small intervals provide underwear-like visual appearance in the waist region of the back body panel.

The sixth elastic region may comprise 7 to 15 elastic threads. The relatively large number of elastic threads enables a large and comfortable back portion.

The sixth elastic region may comprise a plurality of elastic threads arranged parallel at substantially equally spaced intervals of 5 to 13 millimetres. Having relatively large intervals between neighbouring elastic threads in the back portion of the absorbent article enables a large and comfortable back portion.

The third elastic region may comprise 4 to 9 elastic threads. Since the third elastic region extends over a large area, i.e. over the buttocks-covering section and overlapping with the first and second elastic regions, relatively many elastic threads are required for high level of comfort and fit.

The third elastic region may comprise a plurality of elastic threads arranged parallel at substantially equally spaced intervals of 10 to 30 millimetres. Relatively large intervals in the buttocks-covering section provide generous fit and flexibility.

The absorbent article may further comprise an elastic leg feature fastened adjacent the leg edges of the back body panel. A distinct leg elastic of the back body panel typically results in improved comfort, fit and discrete underwear-like visual appearance.

The length of the intervals in the longitudinal direction between neighbouring elastic threads may be larger in the second elastic region than in the first and/or fourth elastic regions. The second elastic region, which also may be referred to as the belly region, typically provides good fit and comfort with less contractile force per unit area than the first and/or fourth elastic regions, i.e. waist and leg elastic regions. Larger interval typically results in less contractile force per unit area.

The length of the intervals in the longitudinal direction between neighbouring elastic threads may be larger in the third elastic region than in the sixth elastic region. The third elastic region, which extends into the buttocks-covering section, generally requires less contractile force per unit area than the sixth elastic region for enabling desired fit and comfort and generous space of the buttocks. Larger interval typically results in less contractile force per unit area.

The length of the intervals in the longitudinal direction between neighbouring elastic threads may be larger in the sixth elastic region than in the fifth elastic region. The relatively small intervals in the fifth elastic region provide underwear-like visual appearance in the waist region of the back body panel.

A contractile force per unit area may be smaller in the second elastic region than in the first and/or fourth elastic regions. The second elastic region, which also may be referred to as the belly region, typically provides good fit and comfort with less contractile force per unit area than the first and/or fourth elastic regions, i.e. waist and leg elastic regions A contractile force per unit area may be smaller in the third elastic region than in the sixth elastic region. The third elastic region, which extends into the buttocks-covering section, generally requires less contractile force per unit area than the sixth elastic region for enabling desired fit and comfort and generous space of the buttocks of a user.

A contractile force per unit area may be smaller in the sixth elastic region than in the fifth elastic region. The relatively high contractile force per unit area in the fifth elastic region provides underwear-like visual appearance in the waist region of the back body panel.

A contractile force per unit area may be smaller in the third elastic region than in the first and/or second elastic regions. This relationship illustrates the generous and comfortable fit of the buttocks-covering section compared with the leg and belly elastics of the front body portion, which relationship results in improved comfort and fit of the absorbent article.

The front body panel may be gathered in a natural state of the absorbent article caused by the gathering effect of the elastic threads, wherein the gathered material of the front body panel may comprise substantially longitudinally extending peaks separated by substantially longitudinally extending valleys, wherein a length of 200 millimetres of the first and/or fourth elastic regions of the gathered panel as measured in an extended state of the absorbent article may comprise about 35 to 55 peaks, specifically 40 to 50 peaks, as measured in a natural state of the absorbent article. This relatively high number of peaks per 200 millimetres in stretched state provides a very smooth and underwear-like visual appearance of the first and/or fourth elastic regions, i.e. leg and waist elastics of the front body panel.

The front body panel may be gathered in a natural state of the absorbent article caused by the gathering effect of the elastic threads, wherein the gathered material of the front body panel may comprise substantially longitudinally extending peaks separated by substantially longitudinally extending valleys, wherein a length of 200 millimetres of the second elastic region of the gathered panel as measured in an extended state of the absorbent article may comprise about 15 to 30 peaks, specifically 18 to 25 peaks, as measured in a natural state of the absorbent article. This value, which is about half of the number of peaks in the first and/or fourth elastic region, indicates that the contractile force per unit area is lower in the second elastic region than the first and/or fourth elastic regions, and this enables good fit and comfort in the belly portion of the front body panel.

Further advantages and advantageous features of the disclosure are provided in the following detailed description.

BRIEF DESCRIPTION OF THE DRAWINGS

With reference to the appended drawings, below follows a more detailed description of the disclosure.

In the drawings:

FIG. 1 shows a perspective view of the absorbent article according to the disclosure, FIG. 2 shows the absorbent article of FIG. 1 in disassembled flat state, FIG. 3 show the absorbent article of FIG. 1 with the elastic regions marked, FIG. 4 shows a schematic geometrical shape of the back body panel, FIG. 5 shows a side view of the absorbent article of FIG. 1, FIG. 6A shows a front view of the laminated web material of the front body panel, FIG. 6B shows the section A-A indicated in FIG. 6A, FIG. 7 shows a flat-front absorbent article in disassembled flat state, and FIG. 8 shows the absorbent article of FIG. 7 in a front perspective view.

DETAILED DESCRIPTION OF PARTICULAR EMBODIMENTS

Various aspects of the disclosure will hereinafter be described in conjunction with the appended drawings to illustrate and not to limit the disclosure, wherein like designations denote like elements, and variations of the described aspects are not restricted to the specifically shown embodiments, but are applicable on other variations of the disclosure.

In FIG. 1 of the drawings an example embodiment of a disposable pant-type absorbent article 1 specially adapted for an adult user is schematically illustrated in an assembled and ready-to-use state. The pant-type absorbent article 1 is for example pant diaper, a sanitary pant or an incontinence pant adapted for use of an adult male or female user. The pant-type absorbent article 1 according to the example embodiment of FIG. 1 comprises a dual-piece chassis having a front body panel 3, a back body panel 4 and an absorbent insert 2 located mainly in a crotch portion of the absorbent article 1 and connected to interior side of the front and back body panels 3, 4 for bridging the gap between the front and back body panels 3, 4. The absorbent insert 2 comprises an absorbent core 5 for absorbing body fluid.

In short, manufacturing of the pant-type absorbent article is performed by first manufacturing two parallel continuous strips of laminated elastic web material that should form the front and rear body panels 3, 4 of the finished absorbent article 1.

Manufacturing of the laminated elastic web material of the front and rear body panels 3,4 are typically performed by feeding a first and a second continuous substantially non-elastic sheet of web material, such as for example a substantially non-elastic nonwoven material, along a machine direction, while simultaneously feeding a plurality of continuous elastic threads arranged parallel with one another. Subsequently, the first and second sheets of web material are joined to each other with a plurality of continuous elastic threads located between the first and second sheets.

The elastic threads are attached to the first and second sheets in a tensioned state and parallel with the web material. Elastic threads arranged parallel with the machine direction, i.e. in the transverse direction X, may for example have adhesive applied thereto before being fastened in a tensioned state to the web material. Alternatively, the web material itself may have adhesive applied to it for securing the elastic threads thereto. The latter is particularly advantageous when the elastic threads exhibit a curved orientation over the transverse length of the absorbent article 1. The finished laminated elastic web will consequently gather when allowing the elastic threads to return to their natural state.

However, while still keeping the elastic threads in tensioned state the method further comprises a step of placing a finished absorbent insert 2 in the gap between the two parallel continuous strips of laminated elastic web, such that the absorbent insert 2 partly overlaps with the both said strips, and subsequently securing the absorbent insert 2 to said strips. The absorbent insert 2 is thus manufactured separately from the front and back body panels 3, 4 and subsequently placed and fastened to said body panels 3, 4 in a suitable manufacturing step.

The manufacturing method may optionally include step of providing a flat front and/or flat back design. This would involve having the elastic threads free of adhesive in a central area of the front and/or rear body panel and performing an interrupting operating of the elastic threads located in the central portion of the front and/or rear body panel, such that the portion of the elastic threads located in the central portion of the front and/or rear body panel 3, 4 and are free from adhesive are allowed to return to their natural, un-tensioned, state without exerting a gathering effect on the surrounding web material, thereby creating a flat area at a desired region of the front and/or rear body panel 3, 4. Such a flat area is typically desirable in the area where the absorbent core 5 overlaps the front and/or rear body panels 3, 4 because the gathering effect of active elastic threads on the absorbent core 5 may be deemed having a negative effect on the absorption capacity of the absorbent core 5.

After securing the absorbent insert 2 to the two parallel continuous strips of laminated elastic web the entire continuous material band is folded at a fold line extending substantially in the transverse direction X of the absorbent insert 2, such that the two parallel continuous strips of laminated elastic web becomes superposed after folding. Thereafter the two parallel continuous strips of laminated elastic web are joined to each other at discrete locations at predetermined fixed intervals along the material band using for example ultrasonic welding, to form side seams 6a, 6b of the finished absorbent article 1. Consequently, side edges of the front body panel 3 are permanently attached to opposite side edges of the back body panel 4 to form side seams 6a, 6b of the finished and assembled absorbent article 1, thereby also defining a waist-opening 7 and a pair of leg-openings 8.

In a final step the continuous material band is cut in a machine cross direction in the area in or adjacent to the side seams 6a, 6b to transform the folded continuous material band into individual absorbent articles 1. When the laminated elastic web material of the front and back body panels 3, 4 is no longer held in stretched state in the transverse direction X the sandwiched elastic threads will cause the web material to gather, i.e. to contract in the transverse direction X and to form small undulations in the laminated elastic web material. An example manufacturing process for such an elastic web material is described more in detail in document WO2014098683 A1, which is referred to in its entirety.

In FIG. 2 of the drawings the same example embodiment of the disposable pant-type absorbent article 1 is schematically illustrated in flat, non-assembled state, and without opposite side edges 9a, 9b, 10a, 10b of the front and back body panels 3, 4 being attached to each other in side seams 6a, 6b. This may for example be realised by breaking the side seams 6a, 6b of a finished absorbent article 1 and unfolding the pant-type absorbent article 1 into a flat state. The pant-type absorbent article 1 comprises, in an unfolded and flat state, a longitudinal direction Y that is substantially parallel with a direction of elongation of the absorbent insert 2. The transverse direction X is perpendicular to the longitudinal direction Y.

The pant-type absorbent article 1 of the example embodiment illustrated in FIG. 1 and FIG. 2 comprises a front body panel 3 having a waist edge 20, a pair of leg edges 21a, 21b and a pair of side edges 9a, 9b. The front body panel 3 has a substantially rectangular shape, and the total length 22 of the front body panel 3 in the transverse direction X is typically in the range of about 550-790 mm and the total length 23 of the front body panel 3 in the longitudinal direction Y is typically in the range of about 140-240 mm, depending on size of the absorbent article 1.

With reference to FIG. 3, which corresponds to FIG. 2 but with the first to sixth elastic regions 11-16 of the absorbent article 1 marked, the front body panel 3 has a first elastic region 11 extending along the leg edges 21a, 21b of the front body panel 3, thereby defining a leg elastic feature. The front body panel 3 further has a second elastic region 12 located next to the first elastic region 11 towards the waist edge 20 of the front body panel 3. The second elastic region 12 may be referred to as an elastic belly region because it may, depending on the size of the second elastic region 12, extend over the belly of a user.

The front body panel 3 further has a fourth elastic region 14 extending along the waist-edge 20 of the front body panel 3, and the second elastic region 12 is located between the first and fourth elastic regions 11, 14. Said first, second and fourth elastic regions 11, 12, 14 are schematically illustrated in FIG. 3, which corresponds to the unfolded absorbent article of FIG. 2.

The size or length 11L of the first elastic region may be in the range of about 5 to 20 mm, specifically about 8 to 17 millimetres, as seen in the longitudinal direction Y.

The size 12L of the second elastic region 12 may be in the range of about 70 to 190 mm, specifically about 100 to 160 millimetres, as seen in the longitudinal direction Y.

The size 14L of the fourth elastic region 14 may be in the range of about 5 to 20 mm, specifically about 8 to 17 millimetres, as seen in the longitudinal direction Y.

Each of the first, second and fourth elastic regions 11, 12, 14 are elasticised by means of a plurality of elastic threads 11T, 12T, 14T arranged substantially in the transverse direction X across a major portion of the front body panel 3. The individual parallel elastic threads 11T, 12T, 14T extend from a location adjacent one side edge 9a of the front body panel 3 to a location adjacent the other side edge 9b of the front body panel 3.

Since it may be advantageous to have the side seams 6a, 6b free from adhesive the continuous elastic threads will in the area of the side seam 6a, 6b during manufacturing of the absorbent article 1 snap back upon the cutting operation required for splitting the continuous material band into individual absorbent articles. Therefore a narrow longitudinal strip 24a, 24b of material is illustrated having no elastic threads attached thereto in FIG. 2. Therefore, the first, second and fourth elastic regions 11, 12, 14 do not necessarily extend out to the edge 9a, 9b of the front body panel 3, as shown in FIG. 3.

In the disclosed example embodiment of FIG. 1 and FIG. 2 the elastic threads 11T, 12T, 14T extend substantially parallel with the transverse direction X, but they may alternatively locally exhibit a small inclination with respect to the transverse direction X, for example if the front body panel 3 has shape different from a rectangle.

The first elastic region 11 may comprise 4 to 6 elastic threads. Moreover, the first elastic region 11 may comprise a plurality of elastic threads 11T arranged in parallel at substantially equally spaced intervals of 2 to 8 millimetres. Each of the elastic threads 11T in the first elastic region 11 may have substantially equal mass density, which for example may lie in the range 600 to 1000 decitex, specifically in the range of 750 to 850 decitex.

The second elastic region 12 may comprises 9 to 18 elastic threads 12T. Moreover, the second elastic region 12 may comprises a plurality of elastic threads 12T arranged in parallel at substantially equally spaced intervals of 5 to 13 millimetres. Each of the elastic threads 12T in the second elastic region 12 may have substantially equal mass density, which for example may lie in the range 350 to 750 decitex, specifically in the range of 500 to 600 decitex.

The fourth elastic region 14 may comprises 4 to 6 elastic threads 14T. Moreover, the fourth elastic region 14 may comprise a plurality of elastic threads 14T arranged in parallel at substantially equally spaced intervals of 2 to 8 millimetres. Each of the elastic threads 14T in the fourth elastic region 14 may have substantially equal mass density, which for example may lie in the range 600 to 1000 decitex, specifically in the range of 750 to 850 decitex.

The length of the intervals in the longitudinal direction between neighbouring elastic threads is preferably larger in the second elastic region 12 than in the first and/or fourth elastic regions 11, 14.

Furthermore, a contractile force per unit area may be smaller in the second elastic region 12 than in the first and/or fourth elastic regions 11, 14. This is the result of the desire of having a discrete underwear-like visual appearance with the distinct waist and leg edges, as well as improved comfort and fit.

The pant-type absorbent article 1 of the example embodiment illustrated in FIG. 1 and FIG. 2 further comprises a back body panel 4 having waist edge 25, a pair of leg edges 27a, 27b, a pair of side edges 10a, 10b, a main section 28 and a buttocks-covering section 29.

The back body panel 4 may, as schematically illustrated in FIGS. 1 and 2, have a shape composed of a substantially rectangular shaped main section 28 intended to be located towards a waist of a user and a substantially trapezoid shaped buttocks-covering section 29 intended to be located towards a crotch of a user. The geometry of the substantially rectangular main section 28 and substantially trapezoid shaped buttocks-covering section 29 are further schematically shown in FIG. 4. A certain level of variations in said schematic geometry is of course possible. For example, the side edges of said sections 28, 29 may for example be non-linear, the corners may be more rounded, the total length of the buttocks-covering section 29 in the transverse direction X may be smaller than the total length of the main section 28 in the transverse direction X, etc.

In the example embodiment of FIGS. 1 to 3 the main section 28 of the back body panel has shape that substantially corresponds to the rectangular-shaped front body panel 3. In other words, the length 30 of the main section 28 of the back body panel 4 in the longitudinal direction Y is substantially equal to the length 23 of the rectangular-shaped front body panel 3 in the longitudinal direction Y, and the length 31 of the main section 28 of the back body panel 4 in the transverse direction X is substantially equal to the length 22 of the rectangular-shaped front body panel 3 in the transverse direction X.

According to a further example embodiment, the length 30 of the main section 28 of the back body panel 4 in the longitudinal direction Y may substantially equal to the length 23 of the side seam 6a, 6b in the longitudinal direction Y.

A length 32 of the buttocks-covering section 29 in the longitudinal direction Y may be in the range of 25 to 60%, specifically 35% to 50%, of the maximal length 33 of the back body panel 4 in the longitudinal direction Y. The maximal length 33 of the back body panel 4 in the longitudinal direction may be about 270-370 mm, depending in size of the absorbent article 1. Moreover, the maximal length 32 of the buttocks-covering section 29 in the longitudinal direction Y may be about 100-160 mm, depending in size of the absorbent article 1.

The back body panel 4 has a third elastic region 13 extending partly over the buttocks-covering section 29 and partly over the main section 28. The third elastic region 13 may comprise 4 to 9 elastic threads 13T. Moreover, the third elastic region 13 may comprise a plurality of elastic threads 13T arranged in parallel at substantially equally spaced intervals of 10 to 30 millimetres. Each of the elastic threads 13T in the third elastic region 13 may have substantially equal mass density in the range 350 to 750 decitex, specifically in the range of 500 to 600 decitex.

The back body panel 4 may further comprise a fifth elastic region 15 extending along the waist-edge 25 of the back body panel 4. The fifth elastic region 15 may comprise 4 to 6 elastic threads 15T. Moreover, the fifth elastic region 15 may comprise a plurality of elastic threads 15T arranged parallel at substantially equally spaced intervals of 2 to 8 millimetres. Each of the elastic threads 15T in the fifth elastic region 15 has substantially equal mass density in the range 600 to 1000 decitex, specifically in the range of 750 to 850 decitex.

The back body panel 4 may further have a sixth elastic region 16 located between the third and fifth elastic regions 13, 15. The sixth elastic region 16 may comprise 7 to 15 elastic threads 16T. Moreover, the sixth elastic region 16 comprises a plurality of elastic threads 16T arranged in parallel at substantially equally spaced intervals of 5 to 13 millimetres. Each of the elastic threads 16T in the sixth elastic region 16 has substantially equal mass density in the range 350 to 750 decitex, specifically in the range of 500 to 600 decitex.

Each of the third, fifth and sixth elastic regions 13, 15, 16 of the back body panel 4 are elasticised by means of a plurality of elastic threads 13T, 15T, 16T arranged substantially in the transverse direction X across a major portion of the back body panel 4. The individual parallel elastic threads 13T, 15T, 16T extend from a location adjacent one side edge 10a of the back body panel 4 to a location adjacent the other side edge 10b of the back body panel 4.

The size or length 13L of the third elastic region 13 may be in the range of about 5 to 20 mm, specifically about 8 to 17 millimetres, as seen in the longitudinal direction Y.

The size 16L of the sixth elastic region 16 may be in the range of about 70 to 190 mm, specifically about 100 to 160 millimetres, as seen in the longitudinal direction Y.

The size 15L of the fifth elastic region 15 may be in the range of about 5 to 20 mm, specifically about 8 to 17 millimetres, as seen in the longitudinal direction Y.

The length of the intervals in the longitudinal direction Y between neighbouring elastic threads may be larger in the third elastic region 13 than in the sixth elastic region 16. This is the result of the desire to have a more flexible and generous fit in the buttock-covering section 29, as well as in the lower part of the main section 28.

Furthermore, the length of the intervals in the longitudinal direction Y between neighbouring elastic threads is larger in the sixth elastic region 16 than in the fifth elastic region 15. This is the result of the desire of having a discrete underwear-like visual appearance with the distinct waist.

In addition, the absorbent article 1 of FIG. 1-3 further comprises an elastic leg feature 34 fastened adjacent the leg edges 27a, 27b of the back body panel 4. The elastic leg feature 34, which typically comprises about 2-6 individual parallel elastic threads, follows the leg edges 27a, 27b of the buttocks-covering section 29.

The longitudinal extension or length 11L-16L of any individual elastic region 11-16 having a plurality of elastic threads 11T-16T arranged in parallel in the transverse direction X across a major portion of the front or back body panel 3, 4, corresponds to the maximal distance in the longitudinal direction Y between the two outermost elastic threads of a set of neighbouring elastic threads each having substantially uniform characteristic. The uniform characteristic of the elastic threads in a certain elastic region may be having equal interval between neighbouring threads, thereby distinguishing from a neighbouring elastic region having a different interval between neighbouring elastic threads. Alternatively, the uniform characteristic the elastic threads in a certain elastic region may be having equal mass density, thereby distinguishing from a neighbouring elastic region having a different mass density of the elastic threads. According to still a further alternative, the uniform characteristic of the elastic threads in a certain elastic region may be a specific level of elastic stretching of the elastic threads during manufacturing, thereby distinguishing from a neighbouring elastic region having a different specific level of elastic stretching of the elastic threads during manufacturing.

A side edge 13L1 of the third elastic region 13 in the area of the side seams 6a, 6b overlaps in the longitudinal direction Y both a side edge 11L of the first elastic region 11 and part of a side edge 12L of the second elastic region 12, in the finished and assembled state of the absorbent article. This overlap enables a relatively large third elastic region 13, and the relatively large elasticity and flexibility typically associated with the buttocks-covering section 29 will seamlessly extend into the main section 28 of the back body panel 4, thereby resulting in improved comfort and fit.

This overlap is further identified in FIG. 5, which schematically illustrates the finished ready-to-use pant type absorbent article of FIG. 1 but illustrated from the side, i.e. facing a side seam 6b.

The side edge 13L1 of the third elastic region 13 at the side seams 6a, 6b overlaps about 15 to 80 millimetres, specifically about 25 to 65 millimetres, as seen in the longitudinal direction Y, with the side seams 6a, 6b of the absorbent article 1.

Moreover, a side edge 13L2 of the third elastic region 13 extends about 15 to 80 millimetres, specifically about 25 to 65 millimetres, as seen in the longitudinal direction Y, into the buttocks-covering section 29.

The relatively large elasticity and flexibility typically associated with the buttocks-covering section 29 results in a smaller contractile force per unit area in the third elastic region 13 than in the neighbouring sixth elastic region 16. Moreover, since the contractile force per unit area is smaller in the sixth elastic region 16 than in the fifth elastic region 15, a gradually decreasing contractile force per unit area will be attained from a waist, edge 25 towards a crotch side of the back body panel 4.

Moreover, the relatively large elasticity and flexibility typically associated with the buttocks-covering section 29 also renders the contractile force per unit area of the third elastic region 13 to be smaller than contractile force per unit area of the first and/or second elastic regions 11, 12. This relationship illustrates the generous and comfortable fit of the buttocks-covering section 13 compared with the first and second regions 11, 12 associated with the leg and belly elastics of the front body portion 3, which relationship results in improved comfort and fit of the absorbent article 1.

For the purpose of avoiding too high compression of the absorbent core 5 the sixth elastic region 16 does preferably not overlap with the absorbent core 5 more than 40 millimetres in the longitudinal direction Y, specifically not more than 20 millimetres. According to an example embodiment, the third elastic region 13 is selected for overlapping the absorbent core due to the lower contractile force per unit area of the third elastic region 13.

FIG. 6A schematically illustrates front view of a small portion of the laminated elastic web 63 of the front body panel 3 in a natural and relaxed state. The laminated elastic web of the front body panel 3 will gather and contract when allowing the elastic threads to return to their natural state. In said gathered state the gathered material of the front body panel 3 comprises substantially longitudinally extending peaks 61 separated by substantially longitudinally extending valleys 62. FIG. 6B schematically illustrates section A-A of the laminated elastic web 63 comprising the peaks 61 separated valleys 62. If a section of the front body panel 3 is stretched to the extended state, and the end points of a 200 mm long section in the transverse direction X of said stretched front body panel 3 is marked, and the front body panel 3 subsequently is allowed to return to its natural gathered state again, the first and/or fourth elastic regions 11, 14 of the gathered front body panel 3 will comprises about 35 to 55 peaks, specifically 40 to 50 peaks, in the area between the marked end points, as measured in a natural state of the absorbent article 1.

Similarly, if a section of the front body panel 3 is stretched to the extended state, and the end points of a 200 mm long section in the transverse direction X of said stretched front body panel 3 is marked, and front body panel 3 subsequently is allowed to return to its natural gathered state again, the second elastic region 12 of the gathered front body panel 3 will comprises about 15 to 30 peaks, specifically 18 to 25 peaks, as measured in a natural state of the absorbent article 1.

These parameters describe that the first and fourth elastic regions 11, 14, which are associated with the waist and leg edges 20, 21a, 21b of the front body panel 3, have a much finer creasing than the centrally arranged second elastic region 12. This setup thus contributes towards providing a pant type absorbent article with improved comfort, fit and discrete underwear-like visual appearance.

According to an alternative example embodiment the pant type absorbent article 1 according to the disclosure may be provided with a so called flat-front design and/or flat-back design. This expression herein refers to a design of the absorbent article 1 where at least a portion of the elastic threads 11T-16T extending in a substantially transverse direction X over the front and/or back body portion 3, 4 are interrupted in a central region 65 of the front and/or back body panel 3, 4, as illustrated in FIGS. 7 and 8, which illustrates the same absorbent article in disassembled, flat state and finished ready-to-use state, respectively. The elastic threads 11T-13T within the central region 65, such as the elastic threads 11T-13T of the first, second, third elastic regions 11-13, and possibly also the elastic leg feature 34 of the back body panel 4, may lack sufficient adhesive for enabling the elastic threads to gather the sheets of web material making up the front portion in case the elastic threads are cut of in the central region 65. Instead, upon cutting of the elastic threads within a centre region 65 the elastic thread within the area of insufficient adhesive will snap back to a natural, un-stretched, state. The snapped back un-stretched elastic portion 66 of the threads may thus hang loose within the elastic laminated web, while the remaining portion 67 of the elastic thread, where sufficient amount of adhesive is provided to enable the elastic thread to exert a gathering effect, will remain connected to the sheets of web material.

An elastic region 11, 12, 13 having one or more elastic threads that have been interrupted in a central portion 65 is consequently referred to herein as being partly elastic, because said elastic region is still elastic in a major portion thereof, i.e. at the side portions of said regions outside of the central portion 65.

The cutting or breaking of the elastic threads 11T-13T along for example a longitudinal centre line 68 of the absorbent article 1 may for example be performed with a suitable machine during the manufacturing of the absorbent article. The removal of the gathering effect otherwise caused by the elastic threads 11T-13T in the centre region 65 results in a more smooth and flat appearance of the centre region 65 of the absorbent article 1, which is desirable for avoiding unnecessary compression of the absorbent core 5, as well as providing the user with a more cloth-like undergarment appearance and the associated sense of comfort. Obviously, the absorbent article may be provided with a flat-front design, a flat-back design, or both a flat-front and flat-back design.

The term "extended state of the absorbent article" is herein defined as a state in which the absorbent article 1 has been extended in all four direction to such an extent that all the elastic threads contained therein are extended to such an extent that they no longer gather any part of the product, but the entire absorbent article is completely flat and in an un-gathered state. The article is extended only to such an extent that this flat condition is reached.

The term "active elastic thread" refers to piece of elastic web material that includes an elastic thread that has been has been attached to said piece of elastic web material in a tensioned state, such that the piece of elastic web material gathers upon releasing the tensioning of the elastic thread. A piece of web material having an active elastic thread is elasticised, whereas a piece of elastic web material lacking an active elastic thread, e.g. maybe including a passive elastic thread, is not elasticised.

By "absorbent article" is meant an article that absorbs or is adapted to absorb bodily fluids, such as urine and/or blood.

The nonwoven material layers or webs of the present disclosure forming the front and back body panels may for example be selected from, for example, of spunbond, air laid, wet laid, carded, electro spunned or meltblown nonwovens. The nonwoven material may be bonded by multiple techniques, e.g. by needling, hydroentangling, or heat bonding.

The nonwoven material of the disclosed products is a mixture of natural and synthetic materials. Natural fibres are for instance cellulosic fibres or fibres from regenerated cellulose.

The term "elastic thread" is intended to mean an elastic strand or elastic thread which is made of elastic material, such as e.g. natural or synthetic rubber, thermoplastic elastomers, such as thermoplastic polyurethane or styrene block co-polymers or elastane, also referred as to spandex (polyurethane-polyurea copolymer). The threads may be of the elastane type that is available under the trade name "LYCRA", but any suitable elastic thread may be used. The threads may have a linear mass density, dtex, of about 80-1200 dtex.

The elastic threads are elongated during the production process from about 50 to about 300% of the initial, non-tensioned original length, more preferably 100-250% and most preferably 150-220% of the initial, non-tensioned original length. The elastic threads should preferably be of a type that are able to tolerate an elongation of at least about 200% without breaking, so that they can be safely used in the production process without risk for breaking.

Further information with respect to material about the elastic web material is disclosed in WO2014098683 A1, which is referred to in its entirety.

The absorbent core may comprise any conventional material suitable for absorbing discharged bodily wastes, such as cellulosic fluff pulp, tissue layers, highly absorbent polymers (superabsorbents), absorbent foam materials including hydrogel-foam material, absorbent nonwoven materials or the like.

The absorbent core may have a liquid permeable topsheet placed on the side intended to face the skin of a user, and a liquid impermeable backsheet placed on the side of the absorbent body intended to face the garment of a user. Generally, the liquid permeable topsheet comprises or consist of a nonwoven material. The topsheet material may further be composed of tow fibres, porous foams, apertured plastic films etc. As mentioned above, the materials suited as topsheet materials should be soft and non-irritating to the skin and be readily penetrated by body fluid, e.g. urine or menstrual fluid, and display low rewetting properties.

The liquid impermeable backsheet may consist of a thin plastic film, e. g. a polyethylene or polypropylene film, a nonwoven material coated with a liquid impervious material, a hydrophobic nonwoven material which resists liquid penetration or laminates of plastic films and nonwoven materials. The backsheet material may be breathable so as to allow vapour to escape from the absorbent body, while still preventing liquids from passing through the backsheet material.

The topsheet and backsheet may be connected to each other for example by adhesive bonding, gluing or welding by heat or ultrasonic. The topsheet and/or the backsheet may further be attached to the absorbent body by any method known in the art, such as adhesive, heat-bonding etc.

The topsheet and backsheet of the absorbent core 5 may extend outwardly beyond the area of the absorbent core, thereby defining an absorbent insert 2 comprising an absorbent core 5. The maximal length 51 of the absorbent core 5 is typically about 80 to 150 mm in transverse direction X, and the maximal length 52 of the absorbent core 5 is typically and 400 to 600 mm in longitudinal direction Y.

The absorbent core 5 may overlap the front body panel 3 with a length 53 of about 50-100 mm. Moreover, the absorbent core 5 may overlap the back body panel 4 with a length 54 of about 200-250 mm. Alternatively, the absorbent core 5 may overlap the main section of the back body panel 4 with a length of about 30-70 mm.

Reference signs mentioned in the claims should not be seen as limiting the extent of the matter protected by the claims, and their sole function is to make claims easier to understand.

As will be realised, the disclosure is capable of modification in various obvious respects, all without departing from the scope of the appended claims. Accordingly, the drawings and the description thereto are to be regarded as illustrative in nature, and not restrictive. It should be understood that the present absorbent articles and its components and methods are not intended to be limited to the particular forms disclosed. Rather, they are intended to include all modifications, equivalents, and alternatives falling within the scope of the claims. They are further intended to include embodiments that may be formed by combining features from the disclosed embodiments, and variants thereof.

The invention claimed is:

1. A disposable pant-type absorbent article, such as a pant diaper, a sanitary pant or incontinence pant, for an adult user, the absorbent article has a longitudinal direction and a transverse direction and comprises:
   a front body panel having a waist edge, a pair of leg edges and a pair of side edges,
   a back body panel having waist edge, a pair of leg edges, a pair of side edges, a main section and a buttocks-covering section, and an absorbent insert located mainly in a crotch portion of the absorbent article and connected to the front and back body panels for bridging the gap between the front and back body panels, wherein the absorbent insert comprises an absorbent core, wherein the front and back body panels are also joined to each other at opposite side edges to at least partly define a waist-opening and a pair of leg-openings, wherein the front body panel has a first at least partly elastic region extending along the leg edges of the front body panel, and a second at least partly elastic region located next to the first elastic region, wherein the back body panel has a third elastic region extending at least partly over the buttocks-covering section of the back body panel, wherein each of said elastic regions are elasticised by means of a plurality of elastic threads arranged substantially in the transverse direction across a major portion of the front or back body panel, and wherein a side edge of the third elastic region overlaps in the longitudinal direction both a side edge of the first at least partly elastic region and part of a side edge of the second at least partly elastic region at the side seams, wherein the back body panel further comprises a fifth elastic region extending along the waist edge of the back body panel and a sixth elastic region located between the third and fifth elastic regions, wherein the length of the intervals in the longitudinal direction between neighbouring elastic threads is larger in the third elastic region than in the sixth elastic region, and the length of the intervals in the longitudinal direction between neighbouring elastic threads is larger in the sixth elastic region than in the fifth elastic region.

2. The disposable pant-type absorbent article according to claim 1, wherein the front body panel further has a fourth elastic region extending along the waist edge of the front body panel, and wherein the second at least partly elastic region is located between the first and fourth elastic regions.

3. The disposable pant-type absorbent article according to claim 2, wherein the fourth elastic region comprises 4 to 6 elastic threads.

4. The disposable pant-type absorbent article according to claim 2, wherein the front body panel is gathered in a natural state of the absorbent article caused by the gathering effect of the elastic threads, wherein the gathered laminated web material of the front body panel comprises substantially longitudinally extending peaks separated by substantially longitudinally extending valleys, wherein a length of 200 millimetres of the first and/or fourth elastic regions of the gathered front body panel as measured in an extended state of the absorbent article comprises about 35 to 55 peaks as measured in a natural state of the absorbent article.

5. The disposable pant-type absorbent article according to claim 1, wherein a side edge of the third elastic region overlaps about 15 to 80 millimetres, as seen in the longitudinal direction, with the side seams of the absorbent article.

6. The disposable pant-type absorbent article according to claim 1, wherein the third elastic region extends about 15 to 80 millimetres, as seen in the longitudinal direction, into the buttocks-covering section.

7. The disposable pant-type absorbent article according to claim 1, wherein a length of the buttocks-covering section in the longitudinal direction is in the range of 25 to 60% of the maximal length of the back body panel in the longitudinal direction.

8. The disposable pant-type absorbent article according to claim 1, wherein the sixth elastic region does not overlap with the absorbent core more than 40 millimetres in the longitudinal direction.

9. The disposable pant-type absorbent article according to claim 1, wherein a side edge of the first at least partly elastic region has an extension of about 5 to 20 millimetres as seen in the longitudinal direction.

10. The disposable pant-type absorbent article according to claim 1, wherein the front body panel has a substantially rectangular shape.

11. The disposable pant-type absorbent article according to claim 1, wherein the back body panel has a shape composed of a substantially rectangular shaped main section intended to be located towards a waist of a user and a substantially trapezoid shaped buttocks-covering section intended to be located towards a crotch of a user.

12. The disposable pant-type absorbent article according to claim 2, wherein the fourth elastic region comprises a plurality of elastic threads arranged parallel at substantially equally spaced intervals of 2 to 8 millimetres.

13. The disposable pant-type absorbent article according to claim 1, wherein the second at least partly elastic region comprises 9 to 18 elastic threads.

14. The disposable pant-type absorbent article according to claim 1, wherein the second at least partly elastic region comprises a plurality of elastic threads arranged parallel at substantially equally spaced intervals of 5 to 13 millimetres.

15. The disposable pant-type absorbent article according to claim 1, wherein the first at least partly elastic region comprises 4 to 6 elastic threads.

16. The disposable pant-type absorbent article according to claim 1, wherein the first at least partly elastic region comprises a plurality of elastic threads arranged parallel at substantially equally spaced intervals of 2 to 8 millimetres.

17. The disposable pant-type absorbent article according to claim 1, wherein the fifth elastic region comprises 4 to 6 elastic threads.

18. The disposable pant-type absorbent article according to claim 1, wherein the fifth elastic region comprises a plurality of elastic threads arranged parallel at substantially equally spaced intervals of 2 to 8 millimetres.

19. The disposable pant-type absorbent article according to claim 1, wherein the sixth elastic region comprises 7 to 15 elastic threads.

20. The disposable pant-type absorbent article according to claim 1, wherein the sixth elastic region comprises a plurality of elastic threads arranged parallel at substantially equally spaced intervals of 5 to 13 millimetres.

21. The disposable pant-type absorbent article according to claim 1, wherein the third elastic region comprises 4 to 9 elastic threads.

22. The disposable pant-type absorbent article according to claim 1, wherein the third elastic region comprises a plurality of elastic threads arranged parallel at substantially equally spaced intervals of 10 to 30 millimetres.

23. The disposable pant-type absorbent article according to claim 1, wherein the absorbent article further comprises an elastic leg feature fastened adjacent the leg edges of the back body panel.

24. The disposable pant-type absorbent article according to claim 1, wherein the length of the intervals in the longitudinal direction between neighbouring elastic threads is larger in the second elastic region than in the first and/or fourth elastic regions.

25. The disposable pant-type absorbent article according to claim 1, wherein a contractile force per unit area is smaller in the second elastic region than in the first and/or fourth elastic regions.

26. The disposable pant-type absorbent article according to claim 1, wherein a contractile force per unit area is smaller in the third elastic region than in the sixth elastic region.

27. The disposable pant-type absorbent article according to claim 1, wherein a contractile force per unit area is smaller in the sixth elastic region than in the fifth elastic region.

28. The disposable pant-type absorbent article according to claim 1, wherein a contractile force per unit area is smaller in the third elastic region than in the first and/or second elastic regions.

29. The disposable pant-type absorbent article according to claim 1, wherein the front body panel is gathered in a natural state of the absorbent article caused by the gathering effect of the elastic threads, wherein the gathered laminated web material of the front body panel comprises substantially longitudinally extending peaks separated by substantially longitudinally extending valleys, wherein a length of 200 millimetres of the second elastic region of the gathered front body panel as measured in an extended state of the absorbent article comprises about 15 to 30 peaks as measured in a natural state of the absorbent article.

* * * * *